US006228354B1

(12) United States Patent
Jeng

(10) Patent No.: US 6,228,354 B1
(45) Date of Patent: May 8, 2001

(54) WATER RESISTANT FILM-FORMING ANTIMICROBIAL SKIN-PREPARATION

(75) Inventor: David K. Jeng, Lisle, IL (US)

(73) Assignee: Allegiance Corporation, McGaw Park, IL (US)

(*) Notice: Subject to any disclaimer, the term of this patent is extended or adjusted under 35 U.S.C. 154(b) by 0 days.

(21) Appl. No.: 09/346,865

(22) Filed: Jul. 2, 1999

(51) Int. Cl.$^7$ .............................. A61K 7/40; A61K 33/18; A61K 47/06; A61K 47/30; A61K 47/48
(52) U.S. Cl. .................................. 424/78.07; 424/78.31; 424/407; 424/672; 514/772.2; 514/772.3; 514/772.6
(58) Field of Search .................................. 424/405, 407, 424/78.07, 672, 78.31; 514/772.2, 772.3, 772.4, 772.5, 772.6

(56) References Cited

U.S. PATENT DOCUMENTS

| | | |
|---|---|---|
| Re. 29,656 | 6/1978 | Chittenden et al. . |
| 4,057,624 | 11/1977 | Hase et al. . |
| 4,128,634 | 12/1978 | Hase et al. . |
| 4,155,663 | 5/1979 | Cerquozz . |
| 4,234,103 | 11/1980 | Strobl, Jr. et al. . |
| 4,415,288 | 11/1983 | Gordon et al. . |
| 4,498,796 | 2/1985 | Gordon et al. . |
| 4,507,111 | 3/1985 | Gordon et al. . |
| 4,542,012 | 9/1985 | Dell . |
| 4,584,192 | 4/1986 | Dell et al. . |
| 4,898,293 | 2/1990 | Morel . |
| 4,925,327 | 5/1990 | Wirt . |
| 4,976,379 | 12/1990 | Sloan . |
| 4,978,527 | 12/1990 | Brink et al. . |
| 5,013,763 | 5/1991 | Tubesing et al. . |
| 5,042,690 | 8/1991 | O'Meara . |
| 5,071,648 | 12/1991 | Rosenblatt . |
| 5,089,606 | 2/1992 | Cole et al. . |
| 5,118,508 | 6/1992 | Kikuchi et al. . |
| 5,120,301 | 6/1992 | Wu . |
| 5,137,718 | 8/1992 | Gillespie . |
| 5,160,737 * | 11/1992 | Friedman et al. ................. 424/401 |
| 5,173,291 | 12/1992 | Brink et al. . |
| 5,288,159 | 2/1994 | Wirt . |
| 5,288,493 | 2/1994 | Martino et al. . |
| 5,376,366 | 12/1994 | Petchul et al. . |
| 5,380,523 * | 1/1995 | Digenis et al. ................. 424/78.25 |
| 5,438,076 * | 8/1995 | Friedman et al. ................. 514/772.6 |
| 5,446,070 | 8/1995 | Mantelle . |
| 5,492,692 * | 2/1996 | Digenis et al. ................. 424/78.25 |
| 5,508,024 | 4/1996 | Tranner . |
| 5,512,055 * | 4/1996 | Domb et al. ................. 604/265 |
| 5,597,561 | 1/1997 | Kross . |
| 5,607,699 | 3/1997 | Hoang et al. . |
| 5,609,763 * | 3/1997 | Boschetti et al. ................. 210/502.1 |
| 5,629,006 | 5/1997 | Hoang et al. . |
| 5,648,399 * | 7/1997 | Friedman et al. ................. 514/772.6 |
| 5,674,513 | 10/1997 | Synder, Jr. et al. . |
| 5,695,458 * | 12/1997 | Shikani et al. ................. 604/4 |
| 5,713,843 | 2/1998 | Vangness . |
| 5,763,412 | 6/1998 | Khan et al. . |
| 5,769,552 | 6/1998 | Kelley et al. . |
| 5,916,822 | 6/1999 | Jeng . |
| 5,916,882 * | 6/1999 | Jeng ................................ 514/57 |
| 5,922,314 | 7/1999 | Hoang et al. . |

FOREIGN PATENT DOCUMENTS

98/23291 * 6/1998 (WO) .

OTHER PUBLICATIONS

Journal: AM. J. Infect. Control, Huang Y.; Oie S.; Kamiya A., Comparative effectiveness of hand–cleansing agents for removing methicillin–resistant *Staphylococcus aureus* from experimentally contaminated fingertips, 1994, pp. 3–4.

Association for Professionals in Infction Control and Epidemiology, Inc. Jeng David K. & Severin Jane E., Povidone iodine gel alchol: A 30–second, onetime application preoperative skin preparation, Oct. 1998, vol. 26, No. 5.

Disinfectants and Antiseptics. A. By Chemical Type, E.L. Larson and H.E. Morton, Alcohols, Chapter 11, pp. 191–203.

Disinfectants and Antiseptics. A. By Chemical Type, W. Gottardi, Iodine and Iodine Compounds, Chapter 8, pp. 152–166.

Proceedings of the International Symposium on Povidone, M. Winicov and E.L. Winicov, Determination of Free Iodine and Its Significance In Poviodone–Iodine Solution, Apr. 17–20, 1983, pp. 186–192.

Complications in Surgery, Richard J. Howard, M.D., Comparision of a 10–Minute Aqueous Iodophor and 2–Minute Water–Insoluble Iodophor Alcohol Preoperative Skin Preparation, Jul. 1991, pp. 43–45.

Clinical Orthopaedics and Related Research, David L. Gilliam, M.D., and Carl L. Nelson, M.D., Comparison of a One–Step Iodophor Skin Preparation Versus Traditioinal Preparation in Total Joint Surgery, Jan. 1990, No. 250 pp. 258–260.

Short Communications, Karen L. Gibson, Alan W. Donald, Harihar Hariharan, and Carole McCarville, Comparison of Two–Pre–Surgical Skin Preparation Techniques, Can J Vet Res 1997; 61:154–156.

(List continued on next page.)

Primary Examiner—Robert H. Harrison
(74) Attorney, Agent, or Firm—Andrew Rozycki; Donald O. Nickey

(57) ABSTRACT

A water-resistant, film-forming topical antimicrobial composition, removable by high pH solution, made in accordance with the principles of the present invention includes a polyvinyl lactam, a broad spectrum antimicrobial agent, a copolymer of polyacrylate/polyoctylacrylamide, a pH sensitive acrylic polymer, and an alcohol. Preferably, the polyvinyl lactam is polyvinyl pyrrolidone. The preferred broad spectrum antimicrobial agent is iodine which is preferably complexed to the polyvinyl pyrrolidone. A process for making the film-forming topical antimicrobial composition is also provided.

143 Claims, No Drawings

OTHER PUBLICATIONS

International Journal of Infectious Diseases, Uda Santos Sanches, PhD; Zella C. Saraiva, M.D.; Teresa C. Tenderio, MS; Judite M. Serra, MS; Don C. Dias, MS; and Herminia de Lencastre, PhD, Extensive Intra–Hospital Spread of a Methicillin–Resistant Staphylococcal Clone, vol. 3, No. 1, Jul.–Sep. 1998, pp. 26–31.

Americna Journal of Medicine, Loreen A. Herwaldt, MD, Control of Methicillin–Resistant *Staphlococcus aureus* in the Hospital Setting, May 3, 1999, vol. 106 (5A), pp. 11s–18s and 48s–52s.

The Pediatric Infectious Disease Journal, Rajesh K. Malik, MD; Marisa A. Monecalvo, MD; Mario R. Reale, MD; Karl LI, MD; Myint Maw, MD et al, Epidemiology and control of vancomycin–resistant enterococci in a regional neonatal intensive care unit, 1999, vol. 18 No. 4, pp. 352–356.

Archives of Biochemistry, Orville Wyss and Frede B. Strandskov, The Germicidal Action of Iodine, pp. 261–26.

Journal of Clinical Microbiology, Ruth L. Berkelman; Betty W. Holland; and Roger L. Anderson, Increased Bacterial Activity of Dilute Preparations of Providone–Iodine Solutions, Apr. 1982, p 635–639.

Journal of Hospital Infection, H. Rackur, New Aspects of mechanism of action of povidone–iodine, 1985, pp. 13–23.

Journal of Hospital Infection, D.J. Leaper, Risk Factors for Surgical Infection, 1995, pp. 127–139.

OR Manager, CDC proposes new surgical site infection guideline, Aug. 1998 vol. 14, No. 8.

Complications in Surgery, Arthur J. Roberts, MD; Kenneth Wilcox, MD; Rajekar Devineni, MD; Ruth B. Harris, Nov./Dec. 1995, pp. 724, 741–744.

Journal of Pharmaceutical Sciences, Hans–Uwe Schenck, Petr Simak, and Erich Haedicke, Strucuture of Polyvinylpyrolidone–Iodine (Povidone–Iodine), 1979, vol. 68, No. 12, pp. 1505–1509.

Journal of Hospital Infection, William Pollack and Oliver Iny, A physico–chemical study of PVP–I solutions leading to the reformulation of Betadine preparations (5% PVP–I), 1985 pp. 25–32.

Thermobacteriology in Food Processing, Stumbo C.R., Death of Bacteria Subjected to Moist Heat, Chapter 7, pp. 70–92.

Degerming Experiments with Aqueous Providone Iodine Containing Disinfecting Solutions: Influence of the Concentration of Free Iodine on the Bactericidial Reaction against *Staphylococcus aureus*, 1986, pp. 372–380, W. Gottardi and M. Puritscher.

* cited by examiner

WATER RESISTANT FILM-FORMING ANTIMICROBIAL SKIN-PREPARATION

FIELD OF THE INVENTION

This invention relates to a film forming, water resistant, pH sensitive, water washable, antimicrobial agent useful in preparing human skin for surgical procedures or in treating human skin prior to needle entry. This invention further relates to an antimicrobial agent which is not harmful to the skin yet promotes asepsis on the skin.

BACKGROUND OF THE INVENTION

Pre-operative preparation with topical antimicrobial agent is an important step to reduce infection in surgical wounds. It is accepted medical practice to apply a topical antimicrobial agent to a surgical site or to a needle entry site to reduce the infection rate. Such treatment helps to control the growth of microorganisms in a wound, a surgical incision, or a needle puncture site. Topical antimicrobial agents are also known in the art as skin-preparations when used to prepare human skin for surgical procedures. The term skin-preparation is used herein to generally describe the class of topical antimicrobial agent solutions.

The application of skin-preparations is known in the art. Such skin-preparations have been applied in the form of preoperative skin treatments. Generally, the skin-preparations contain a broad spectrum antimicrobial agent. Iodine and chlorhexidine are well known broad spectrum antimicrobial agents. Skin preparations containing iodine in combination with polymers are also generally known as iodophor skin-preparations. Existing iodophor skin-preparations typically include an iodine-polymer complex, iodide, a surfactant and a buffer system to provide an appropriate pH in an aqueous system. The iodophor skin-preparations will typically contain 7.5% to 10.0%, on a volume per volume ("v/v") basis, of an iodine-polyvinyl pyrrolidone complex. The iodine-polyvinyl pyrrolidone complex is also known as PVP-I. These concentrations of PVP-I are desirable to provide effective and extended killing of microorganisms.

Standard surgical procedures require the surgical site to be disinfected prior to surgery. Effective pre-operative cleansing of the surgical site is critical to reducing the risk of infection to the patient. Pre-operative skin preparation is therefore as important as a prophylactic antibiotic treatment is in control of infection.

Microorganisms on the skin can be transient or resident. Transient microorganisms lie on the surface of the skin, while resident microorganisms are found at deeper sites in the skin, for example, in skin hair follicles. It is desirable to kill microorganisms both at the skin surface and at sites deeper in the skin. It is also desirable to provide both an initial quick kill and retain a long-term residual antimicrobial activity. It is important that the antimicrobial activity be sustained throughout a surgical procedure by a single application of the skin-preparation.

The conventional method of application of a skin-preparation is to pour a skin-preparation of 7.5% v/v PVP-I scrub solution into a tray, saturate a sponge with the skin-preparation in the tray and then apply the saturated sponge to the surface of skin. The skin-preparation is applied from the center to the peripheral areas of the skin site with a circular scrubbing motion for two to five (2–5) minutes. The sponge provides a physical force to spread the skin-preparation evenly and to remove dead skin cells and skin debris thus delivering the skin-preparation to exposed microorganisms. The site is then blotted dry and painted with a 10% v/v PVP-I solution.

Film forming skin-preparations, such as liquids that form a film after evaporation, are also known in the art. One film forming skin-preparation includes acrylic polymers and iodine complexed with polyvinyl pyrrolidone. Alternatively, a polyvinyl pyrrolidone vinyl acetate copolymer with diisocyanate has been used where iodine is complexed with the polyvinyl pyrrolidone component. Another film forming skin-preparation has been made employing a copolymer of the acrylic or methacrylic acid ester of an alkyl alcohol containing a single hydroxyl group with an N-vinyl lactam. In this latter composition, a broad spectrum antimicrobial agent is complexed with the N-vinyl lactam.

Other compositions providing film forming skin-preparations have been tried. One such composition is the reaction product of an isocyanate prepolymer with polyvinyl pyrrolidone, where a chain extender for the two monomers is employed and iodine is complexed to the polyvinyl pyrrolidone portion of the reaction product. Yet another example is an acetalized polyvinyl alcohol which has been complexed with iodine.

Each of the prior art compositions has disadvantages. Many of the prior art skin-preparations are water soluble. Therefore, such topical agents are removed when a wound or surgical site is irrigated during surgery. Some of the prior art skin-preparations are water insoluble and can only be removed by an organic solvent. Therefore, to remove such skin-preparations requires the application of alcohol, for example, to an already tender wound or surgical site.

It would therefore be advantageous to have a skin-preparation which is resistant to water when dry so that it is not removed when a wound or surgical site is sponged or irrigated. It would also be an advantage to have a skin-preparation which may be removed from the wound or surgical site without resorting to the application of an organic solvent such as alcohol. It would be yet a further advantage to have a skin-preparation that presents the above listed advantages and has an efficacy similar to that for water soluble skin-preparations.

SUMMARY OF THE INVENTION

The present invention provides a skin-preparation which does not harm the skin yet promotes asepsis on the skin. The present invention provides a skin-preparation which has a rapid antimicrobial activity when in a liquid form and a sustained antimicrobial activity when dry. The skin preparation of the present invention forms a film on skin that is water resistant and is not readily removed when a wound or surgical site is sponged or irrigated. The film can be removed by an aqueous solution having the proper pH and with the help of physical rubbing. The present invention further provides a skin-preparation which may be removed without resorting to the application of an organic solvent to a wound or surgical site.

The present invention provides a film-forming topical antimicrobial composition that includes but is not limited to a polyvinyl lactam, a broad spectrum antimicrobial agent chemically complexed with the polyvinyl lactam, a water-resistant polymer system, a neutralizer, a pH sensitive polymer, and an alcohol.

DETAILED DESCRIPTION OF THE INVENTION

The skin-preparation of the present invention includes a polymer of an N-vinyl lactam complexed with a broad spectrum antimicrobial agent, a water-resistant polymer system, a pH sensitive polymer, a neutralizer, and an alcohol. The skin-preparation may also include a polyvinyl acetate, a polyvinyl alcohol, or a combination of these two types of chemical compounds.

The polymer of the N-vinyl lactam component, or polyvinyl lactam, is generally employed in the range of from about 1% to about 10% on a weight per volume ("w/v") basis, and preferably from about 2% w/v to about 8% w/v. A copolymer of a polyacrylate and a polyoctylacrylamide forms a water-resistant polymer system that is employed in the range of from about 0.1% w/v to about 10% w/v, and preferably from about 0.5% w/v to about 5% w/v. The pH sensitive polymer is employed in the range of from about 0.1% w/v to about 10% w/v, and preferably from about 0.2% w/v to about 1% w/v. The iodine/polyvinyl lactam complex, copolymer of polyacrylate and polyoctylacrylamide, and pH sensitive polymer are dissolved in an alcohol to make up about a 100 milliliter (mL) volume. The alcohol is generally employed in the range of from about 30% to about 100% concentration, where the balance is water. When used, the polyvinyl acetate, polyvinyl alcohol, or a combination of these two types of chemical compounds, are used in the range of from about 0.1% w/v to about 10% w/v, and preferably from about 0.5% w/v to about 5% w/v. The polyvinyl acetate and polyvinyl alcohol, when used, are added to the polyvinyl lactam, polyacrylate-polyoctylacrylamide copolymer, and the pH sensitive polymer dissolved in alcohol.

N-vinyl lactams may be selected from N-vinyl substituted derivatives of: 3,3-dimethyl-1-pyrrolidone, 4,4-dimethyl-2-pyrrolidone, 3,4-dimethyl-2-pyrrolidone, 3-ethyl-2-pyrrolidone, 3,5-dimethyl-2-pyrrolidone, and N-vinyl pyrrolidone. The preferred N-vinyl lactam is N-vinyl pyrrolidone. Therefore, the preferred polyvinyl lactam is polyvinyl pyrrolidone. Polyvinyl pyrrolidone is generally commercially available and may be obtained, for example, from Mallinckrodt Baker, Inc., Phillipsburg, N.J.

N-vinyl lactams and the related polymers are particularly effective in complexing elemental iodine to form a broad spectrum antimicrobial agent and thus providing an antimicrobial complex for use in a topical antimicrobial agent. The iodine and alcohol perform synergistically to effectively control both transient and resident skin microorganisms.

PVP-I may be prepared by bringing polyvinyl pyrrolidone and iodine into solution. It is believed that the PVP-I complex forms readily under standard conditions. The amount of titratable iodine in a PVP-I complex can be determined using the well known sodium thiosulfate titration method. The PVP-I complex serves as a reservoir of iodine which is released on demand as "free iodine." It is the free iodine, not the titratable iodine, that is the source of the antimicrobial activity.

Generally, PVP-I is used in an amount that ranges from about 2% to about 15% based on the total weight of the skin-preparation. Levels of iodine within the specified range exhibit acceptable antimicrobial activity. The preferred range of iodine is from about 2% to about 10% based on the total weight of the skin-preparation.

Alternately, PVP-I may be obtained, for example, under the trade name POVIDONE-IODINE SOLUTION from Delasco, Council Bluffs, Iowa. Povidone iodine is also available in a solid powder form and is soluble in water or in a mixture of water and alcohol. The concentration of povidone iodine in the formulation is selected to provide effective microorganism control over an extended period of time.

The water-resistant polymer system of the present invention may include a polyacrylate-polyoctylacrylamide copolymer. The water-resistant polymer system may include other copolymers of either a polyacrylate or an octylacrylamide.

Polyacrylates are polymers of an ester or a salt of acrylic acid. Polyacrylates are generally commercially available and may be obtained from, for example, BASF Corporation, Mount Olive, N.J. Polyacrylates are represented by the following chemical formulas.

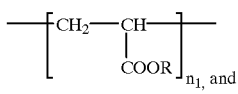

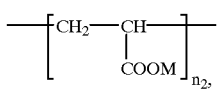

with $n_1$, $n_2$ being from about 2 through about 6000. R substituents include unbranched alkyl, branched alkyl, unbranched alcohol, branched alcohol, ester, ether, or aryl groups. The non-aryl R substituents generally include $C_1$–$C_6$ moieties, and preferably $C_1$–$C_4$ moieties. M is typically a metal selected from Group I of the Periodic Table, and is preferably Na or K. Polyacrylates may also include mixtures of the polymeric ester and the polymeric salt.

Octylacrylamide is an alkyl olefinic acid amide. Generally, octylacrylamide is the isomer 2-ethylhexylacrylamide having the following formula:

However, other structural isomers are possible. A copolymer containing polyacrylates and polyoctylacrylamide is commercially available under the trade name DERMACRYL-79, from National Starch and Chemical Company, Bridgewater, N.J. Such a copolymer is hereinafter referred to as "PA/OAA." However, one of ordinary skill in the art will recognize that other copolymers or blends of polyacrylates and polyoctylacrylamide, generally referred to herein as water-resistant polymer systems, may be used in the composition of the present invention. One such other copolymer is DERMACRYL LT, also commercially available from National Starch and Chemical Company. DERMACRYL LT is a hydrophobic, high molecular weight, carboxylated acrylic copolymer of acrylates and octylacrylamnide. DERMACRYL LT is a white powder having a 3% volatiles content and an acidity of 2.4 meq/g. DERMACRYL LT, is soluble in ethanol, isopropanol and fatty alcohols, but is insoluble in water. DERMACRYL LT can be made water or oil soluble upon neutralization of the carboxyl groups with an appropriate base. Typical bases include triethanolamine, 2-amino-2-methyl-1-propanol, inorganic hydroxides for aqueous solutions, and long chain amines for oil-based solutions.

DERMACRYL 79 is carboxylated and is preferably neutralized with a suitable alkaline material in formulating a skin-preparation. Neutralizers, or bases, such as triethanolamine, 2-amino-2-methyl-1-propanol, ammonium or potassium hydroxides, or long chain amines may be used. Such neutralizers are commercially available under the trade names AMP95 and ARMEEN DM18D, for example, from Angus Chemical Co., Buffalo Grove, Ill. The amount of base required to neutralize the carboxyl groups in DERMACRYL 79, for example, can be determined by the following relationship:

$$B=(W \times 2.4 \times N \times E)/1000$$

where:
B=grams of neutralizer needed
W=grams of DERMACRYL 79 used;
N=%-neutralization required (decimal);
E=equivalent weight of base (eq/g);
The preferred %-neutralization is 0.10 to 0.90.

The pH sensitive polymer may be a pH sensitive acrylic polymer. Such pH sensitive polymers which become soluble either in low pH or in high pH solutions are commercially available under the trade name EUDRAGIT from Hüls America Inc., Somerset, N.J. or from Röhm America, Inc., Piscataway, N.J.

The EUDRAGIT pH sensitive acrylic polymers are aqueous methacrylic polymers that are available in various formulations including formulations expressed in two general series, the "S" series and the "L" series. In the S series, the ratio of carboxyl groups to ester groups is about 1:2. In the L series, the ratio of carboxyl groups to ester groups is about 1:1. Eudragit S is a copolymer of poly(methacrylic acid, methylmethacrylate) at a 1:2 ratio, having a number average molecular weight of about 135,000 (USP Type B). Eudragit L is also a copolymer of poly(methacrylic acid, methylmethacrylate) at a 1:1 ratio; having a number average molecular weight of about 135,000 (USP Type A). The EUDRAGIT S series may be further characterized in that this type of polymer is soluble in an aqueous solution having a pH of 7.0 and above. The EUDRAGIT L series may be further characterized in that this type of polymer is soluble in an aqueous solution having a pH of 5.5 and above. Thus it can be seen that the EUDRAGIT S series polymers are soluble in neutral to basic pH solutions, while the EUDRAGIT L series polymers may be dissolved in acidic solutions. Other pH sensitive polymers will be known to those of skill in the art.

Another aqueous methacrylic polymer, related to those methacrylic polymers disclosed above, may be used to provide sustained release of iodine after the skin-preparation of the present invention has been applied to the skin. Sustained release of iodine may be an advantage in that controlling the release of iodine to the skin over an extended period of time helps to ensure a prolonged source of disinfectant. Sustained release methacrylic polymers are commercially available under the trade name EUDRAGIT RS from Hüls America, Somerset, N.J. or from Röhm America, Inc., Piscataway, N.J. The EUDRAGIT RS aqueous methacrylic polymers are pH insensitive, water insoluble, slightly permeable, non-enteric polymer compounds of acrylic resins comprising copolymers of acrylic and methacrylic esters with a low content of quaternary ammonium groups.

The alcohol may be selected from the group which includes methanol, ethanol, 1-propanol, 2-propanol, 1-butanol, 2-butanol, 1-pentanol, 2-pentanol, and 3-pentanol, and combinations of these alcohols. Typically, the alcohol is a solution containing a mixture of alcohol and water. As described above, the alcohol is used to dissolve the polyvinyl lactam complexed with a broad spectrum antimicrobial agent, a polyacrylate-polyoctylacrylamide copolymer, a neutralizer, and a pH sensitive polymer. The alcohol also provides a rapid and effective initial kill of microorganisms.

Polyvinyl acetate, polyvinyl alcohol, or a combination of these two chemical compounds, may be used to adjust the resistance of the skin-preparation to water. Polyvinyl acetate has the structure:

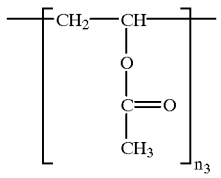

Polyvinyl alcohol, the alcoholysis product of polyvinyl acetate, has the structure:

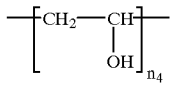

For polyvinyl acetate, $n_3$ may range from about 2 to about 2100, and for polyvinyl alcohol $n_4$ may range from about 2 to about 3400. Preferably, the range of the weight average molecular weight of polyvinyl acetate is between 130,000 to 180,000 and the range of the weight average of the molecular weight of polyvinyl alcohol is between 50,000 to 150,000.

As described above, the composition of the present invention may also contain water. It is preferable that a small quantity of water be used in the composition. The water content may range from about 0% v/v to about 40% v/v. It is preferable that the water content range from about 1% v/v to about 10% v/v.

The skin-preparation may include other components. Chemical buffers may be added to maintain a proper pH level. Also, acids or bases may be added to adjust the pH level. A base, suitable for adjusting the pH may include, for example, alkali metal hydroxides. Suitable alkali metal hydroxides include sodium hydroxide and potassium hydroxide, for example. Acids, suitable for adjusting the pH may include various acids, such as citric acid, lactic acid and acetic acid. The skin-preparation may include components to reduce the potential for skin irritation after the skin-preparation is applied to a wound or surgical site. Such components may include glycerin, petroleum jelly, petrolatum, mineral oil, ethylene glycol, and glycerol, for example.

Additional components can also be added to the skin-preparation as desired. For example, iodide could be added to stabilize the iodine, and a dye could be added to provide a desired color. Fatty acids could be added to increase the time of antimicrobial action by the skin-preparation. Surfactants could also be added to enhance wetting of the wound or surgical site by the skin-preparation.

It is important that skin-preparations provide rapid and prolonged antimicrobial action. This objective is met by formulating the skin-preparation with alcohol, PVP-I, or a similar antimicrobial complex, PA/OAA or a similar water-resistant polymer system, and a pH sensitive polymer. By formulating the skin-preparation with PVP-I and alcohol, for example, the antimicrobial action of iodine and alcohol perform synergistically or complement each other because the iodine and alcohol have different modes of action as antimicrobial agents. The alcohol in the skin-preparation enables the antimicrobial skin-preparation to effectively deliver a rapid action against microorganisms and allows for a reduction in the amount of PVP-I used as compared to non-alcoholic compositions. A lower PVP-I amount tends to reduce skin irritation that may arise through skin contact with the iodophor.

The use of PA/OAA, or similar polymer system, results in a water resistant skin-preparation, once the skin-preparation has dried on a skin surface. The PA/OAA provides an effective barrier that holds the PVP-I component to the skin surface and reduces the likelihood that the skin-preparation will be readily removed, by rubbing for example, from the skin surface.

The pH sensitive polymer further strengthens the water resistance of PA/OAA and aids the removal of the skin preparation from the skin by aqueous solutions having an appropriate pH. Removal of the skin-preparation of the present invention with alcohol is not required, and, accordingly, further irritation of a wound by alcohol is avoided.

When a pH sensitive polymer is selected that will dissolve in a low pH aqueous solution, then a low pH solution such as vinegar and water may be used to remove the skin preparation from the skin. Other low pH solutions may include aqueous solutions of inorganic acids such as hydrochloric acid. Other acidic solutions will be apparent to those skilled in the art. The pH of the low pH solution may range from about 5.5 to about 6.9 and preferably from about 5.7 to about 6.4.

Similarly, when a pH sensitive polymer is selected that will dissolve in a neutral to basic pH aqueous solution, then a solution such as soap and water may be used to remove the skin-preparation from the skin. Other neutral to basic pH solutions may include aqueous solutions of inorganic bases such as sodium hydroxide or potassium hydroxide. Additional solutions will be apparent to those skilled in the art. The pH of the neutral to basic pH solution may range from about 7 to about 10 and preferably from about 7.8 to about 9.3.

The United States Food and Drug Administration ("FDA") has published proposed test methods and performance requirements for healthcare disinfectants, including skin-preparations. The FDA's proposed methods and performance requirements are described in the "Tentative Final Monograph for Health-Care Antiseptic Drug Products" (the "TFM"). Such performance requirements include the TFM "Time-Kill" test, the TFM "Minimum Inhibition Concentration" test, and the TFM "Efficacy" test. Other performance tests may also be used.

The skin-preparation of the present invention has been tested and found to be an effective antimicrobial agent both in vivo and in vitro. The skin-preparation of the present invention exhibited antimicrobial activity equal to or better than the prior art skin preparations. These results are further discussed in the Examples below.

EXAMPLE 1

In a test of in vitro efficacy, the results demonstrate that the skin preparation of the present invention is superior to BETADINE SOLUTION ("BETADINE"), a conventional skin preparation. BETADINE is an aqueous solution of PVP-I and is available from The Purdue Frederick Company, Norwalk, Conn. A 10% solution of BETADINE contains about 10% v/v PVP-I, about 1% glycerin, about 0.25% IGEPAL (IGEPAL is available from Rhone-Poulenc, Inc., North Brunswick, N.J.) and about 88.75% water. A 7.5% solution of BETADINE contains about 7.5% PVP-I, about 1% glycerin, about 0.25% IGEPAL and about 91.75% water. Example 1 is a comparative study of the skin preparation of the present invention and a 7.5% BETADINE control in a microbial TFM Time-Kill test. This test utilized organisms listed in the TFM and other antibiotic resistant species. Clinically significant results were found in 15 seconds and 30 seconds exposures to the skin-preparation of the present invention. In table 1 provided below, the results for the skin preparation of the present invention are identified as "Present Invention," whereas the results for BETADINE are identified as "Control." The microorganisms utilized in the Time Kill test are identified by their formal technical names, and by identification numbers used by American Tissue Culture Collection ("ATCC"), Manassas, Va., for control microorganisms available from ATCC. The microorganisms may also be identified by "Clinical Isolate" number, which refers to microorganisms isolated in the laboratory of Allegiance Healthcare Corporation, Round Lake Beach, Ill. Clinical Isolate numbers refer to the specific isolate used for each microorganism identified with a clinical isolate number.

TABLE 1

| | LOG REDUCTION | | | |
|---|---|---|---|---|
| | 15 second | | 30 second | |
| | Present Invention | Control | Present Invention | Control |
| Staphylococcus aureus (ATCC #6538) | >6.06 | 4.10 | >6.06 | >6.06 |
| Staphylococcus aureus (ATCC #29213) | >5.38 | 1.56 | >5.38 | 1.34 |
| Staphylococcus aureus (ATCC #33591) M,V | >5.98 | 5.23 | >5.98 | >5.98 |
| Staphylococcus aureus (ATCC #33592) G,M | >6.55 | 2.89 | >6.55 | 4.66 |
| Staphylococcus aureus (ATCC #33593) G,M | >6.17 | 5.07 | >6.17 | >6.17 |
| Staphylococcus aureus (ATCC #33594) G | >6.33 | 2.18 | >6.33 | 4.69 |
| Staphylococcus aureus (ATCC #43300) M | >6.25 | 1.72 | >6.25 | 2.72 |
| Staphylococcus aureus (Clinical Isolate #13) | >5.68 | >5.68 | >5.68 | >5.68 |
| Staphylococcus aureus (Clinical Isolate #22) | >6.39 | 1.38 | >6.39 | 3.33 |
| Staphylococcus aureus (Clinical Isolate #25) | >6.65 | 1.81 | >6.65 | 4.24 |
| Staphylococcus aureus (Clinical Isolate #26) | >6.38 | 3.18 | >6.38 | 5.54 |
| Staphylococcus epidermidis (ATCC #12228) | >6.20 | 4.41 | >6.20 | 5.42 |
| Staphylococcus epidermidis (ATCC #51624) M | >5.84 | 4.61 | >5.84 | >5.84 |
| Staphylococcus haemolyticus (ATCC #29970) | >5.40 | 0.05 | >5.40 | 1.03 |
| Staphylococcus hominis (ATCC #27844) | >5.42 | 5.42 | >5.42 | >5.42 |
| Staphylococcus saprophyticus (ATCC #15305) | >5.92 | 0.84 | >5.92 | 2.31 |
| Streptococcus pyogenes (ATCC #19615) | >6.11 | >6.11 | >6.11 | >6.11 |
| Streptococcus pneumoniae (ATCC #6303) | >4.76 | >4.76 | >4.76 | >4.76 |
| Enterococcus faecalis (Clinical Isolate #9) | >5.92 | 0.24 | >5.92 | 0.69 |
| Enterococcus faecalis (Clinical Isolate #10) | >6.14 | 1.26 | >6.14 | 3.35 |
| Enterococcus faecalis (Clinical Isolate #11) | 6.60 | 3.33 | >6.60 | >5.90 |
| Enterococcus faecalis (Clinical Isolate #17) | >6.40 | 5.70 | >6.40 | >6.40 |
| Enterococcus faecalis (Clinical Isolate #19) | >6.47 | 2.42 | >6.47 | 4.75 |

TABLE 1-continued

|  | LOG REDUCTION | | | |
|---|---|---|---|---|
|  | 15 second | | 30 second | |
|  | Present Invention | Control | Present Invention | Control |
| *Enterococcus faecalis* (ATCC #29212) ? | >6.31 | 3.98 | >6.31 | >5.31 |
| *Enterococcus faecalis* (ATCC #51575) G,S,V | >6.11 | 1.71 | >6.11 | >4.04 |
| *Enterococcus faecium* (ATCC #51559) | >5.90 | 0.77 | >5.90 | 1.22 |
| *Micrococcus lureus* (ATCC #7468) | >4.67 | 0.52 | >4.67 | 0.85 |
| *Acinetobacter baumannii* (ATCC #19606) | >5.71 | 2.43 | >5.71 | >5.71 |
| *Enterobacter aerogenes* (ATCC #13048) | >6.18 | >6.18 | >6.18 | >6.18 |
| *Eschericia coli* (ATCC #11229) | >6.00 | 0.85 | >6.00 | >2.27 |
| *Eschericia coli* (ATCC #25922) | >5.45 | >5.45 | >5.45 | >5.45 |
| *Klebsiella pneumoniae* (ATCC #13383) | >6.13 | >6.13 | >6.13 | >6.13 |
| *Klebsiella oxytoca* (ATCC #15764) | >6.12 | 4.26 | >6.12 | >6.12 |
| *Proteus mirabilis* (ATCC #4630)(7002) | >6.32 | >6.32 | >6.32 | >6.32 |
| *Pseudomonas aeruginosa* (ATCC #15442) | >5.81 | >5.81 | >5.81 | >5.81 |
| *Pseudomonas aeruginosa* (ATCC #27853) | >5.81 | >5.81 | >5.81 | >5.81 |
| *Serratia marcescens* (ATCC #14756) | >6.24 | 3.33 | >5.88 | >5.88 |
| *Bacteroides fragilis* (ATCC #25285) | >6.09 | >6.09 | >6.09 | >6.09 |
| *Haemophilis influenzae* (ATCC #19418) | >6.75 | >6.75 | >6.75 | >6.75 |
| *Candida albicans* (ATCC #10231) | >5.12 | 3.00 | >5.12 | >5.12 |
| *Candida tropicalis* (ATCC #750) | >5.29 | 2.42 | >5.29 | 4.64 |

The Control was 7.5 % BETADINE solution. Where indicated, resistance to antibiotics has the following meanings: M = Methicillin; G = Gentamicin; S = Streptomycin; V = Vancomycin

EXAMPLE 2

In Example 2, the in vivo efficacy of the skin preparation of the present invention was determined. Example 2 shows that in a 30 second application, the skin preparation of the present invention delivered a performance on human skin equivalent to a 5 minute application of a conventional skin preparation. As in example 1, the conventional skin preparation was 7.5% BETADINE. Clinical tests were done on groin and abdomen sites of human subjects. Six replicates were performed for each test (N=6). Table 2 provided below presents these results.

TABLE 2

Average Log Reduction of Normal Flora/cm$^2$ skin (N = 6) Testing Site

|  | Present Invention Time After 30 Second Application | | | Control Time After 30 Second Application | | |
|---|---|---|---|---|---|---|
|  | 10 min | 30 min | 6 hr | 10 min | 30 min | 6 hr |
| Groin | 3.00 | 3.75 | 2.76 | 3.84 | 3.83 | 2.63 |
| Abdomen | 2.70 | 3.14 | 2.73 | 2.28 | 2.69 | 2.18 |

EXAMPLE 3

A skin-preparation was produced according to the principles of the present invention. The composition of this skin-preparation is presented in table 3 below and further includes isopropyl alcohol, also known as isopropanol, water, and the pH sensitive polymer EUDRAGIT S-100.

TABLE 3

| COMPONENT | % (w/v) |
|---|---|
| PVP-I | 7.0 |
| PA/OAA | 1.5 |
| EUDRAGITS-100 | 0.5 |

In making the skin-preparation of table 3, the alcohol and water were first mixed forming a solution that was 90–95% alcohol and 10–5% water. Next, the PVP-I, PA/OAA, and EUDRAGIT S-100 were added to the alcohol and water solution. The solution was adjusted by the addition of a neutralizer, and an additional alcohol and water solution, was used to bring the final solution volume to 100 mL.

In a clinical efficacy test, using a human as the subject, the composition of the present invention was tested and compared to the commercially available skin-preparations PREVAIL and DURAPREP. The PREVAIL skin preparation product is available from Allegiance Healthcare Corporation, McGaw Park, Ill., and is an antimicrobial alcohol gel containing PVP-I. The DURAPREP skin-preparation product is available from Minnesota Mining and Manufacturing Corporation, Minneapolis, Minn., and is an antimicrobial alcohol solution containing polymethacrylate, polyacrylates and elemental iodine.

The objective of the study was to test whether the compositions being evaluated still generated free iodine after the skin preparations had dried. It is well known in the art that it is the free iodine that kills the bacteria. Accordingly, free iodine must be released from the dried film onto the skin to demonstrate the antimicrobial activity.

Each of the compositions, the composition of the present invention, the PREVAIL skin-preparation product, and the DURAPREP skin-preparation product, were applied to human skin and allowed to dry. Twelve healthy human volunteers, both men and women, were chosen as the subjects for the evaluation. Each subject had the composition of the present invention, the PREVAIL skin-preparation product, and the DURAPREP skin-preparation product applied to an area of skin on a forearm.

After the compositions being evaluated had dried, a hollow cylinder was then placed over the area of application and pressed to the skin so that a seal was formed around the periphery of the cylinder. The cylinder is a 4 centimeter tall sterile glass cylinder having an inside diameter of 2.2. centimeters. Thus the cylinder defines an area of approximately 3.8 square centimeters on the skin surface. One mL of a solution containing bacteria at $10^8$ cells/mL of the solution was then added into the cylinder and allowed to stand on the area of application for 15 and 30 seconds, respectively.

At the end of a time period, a total of 5 mL of a "neutralizing" solution was added into the cylinder. The bacteria were retrieved by a cup-stripping technique using a stripping solution and a 1-minute scrubbing by a rubber policeman. The stripping solution included 0.1% sodium thiosulfate in a 0.075 molar phosphate buffer, the buffer having a pH 7.0, and 0.1% of POLYSORBATE 80. The stripping solution then was collected and a bioassay was performed.

The purpose of the neutralizing solution was to stop the kill of bacteria by any free iodine present on the area of application. The log reduction in bacteria was then determined by comparing the concentration of bacteria placed on the area of application to the concentration of bacteria surviving at the time the neutralizing solution was added. The following table 4 presents the results of these tests. The composition of the present invention is identified as "Present Invention."

TABLE 4

| | Log Reduction/ml | | | | | |
|---|---|---|---|---|---|---|
| | Present Invention | | PREVAIL | | DURAPREP | |
| Organism | 15 seconds | 30 seconds | 15 seconds | 30 seconds | 15 seconds | 30 seconds |
| E. coli | 4.10 | 4.70 | 6.26 | 6.54 | 0.30 | 0.00 |
| S. aureus | 4.82 | 5.46 | 5.39 | 6.58 | 0.04 | 0.00 |

As the data of the above table illustrates, the composition of the present invention impeded the release of free iodine somewhat but the free iodine released is sufficient to reduce greater than 99.99% of the bacteria. Thus, the skin-preparation of the present invention is efficacious as an antimicrobial skin preparation agent. As demonstrated, the skin-preparation composition of the present invention did not release free iodine as readily as the water soluble PREVAIL skin-preparation product, yet it released more free iodine than the water insoluble DURAPREP skin-preparation. Thus it has been demonstrated that the skin preparation of the present invention serves the purpose of resisting irrigation and yet possesses sufficient antimicrobial activity. Such a feature overcomes the disadvantages of both the PREVAIL skin-preparation product and the DURAPREP skin-preparation product.

Thus it has been disclosed in embodiments and the preferred embodiment of the present invention a film-forming antimicrobial skin preparation. The present invention provides a skin-preparation which does not harm the skin yet promotes asepsis on the skin. The present invention provides a skin-preparation which is resistant to water so that it is not removed when a wound or surgical site is sponged or irrigated. The present invention also provides a skin-preparation which may be removed from the wound or surgical site by washing the site with a water-based solution of specific pH. Thus, the present invention provides a skin-preparation which may be removed without resorting to the application of a solvent such as alcohol. Other embodiments can be easily envisioned within the basic principles of the present invention.

It should be understood that various changes and modifications preferred in the embodiment described herein will be apparent to those skilled in the art. Such changes and modifications can be made without departing from the spirit and scope of the present invention and without demising the attendant advantages. It is therefore intended that such changes and modifications be covered by the appended claims.

What is claimed is:

1. An aqueous solution for use as a water resistant film-forming antimicrobial skin-preparation, the aqueous solution comprising:
    a polyvinyl lactam;
    a broad spectrum antimicrobial agent chemically complexed with the polyvinyl lactam;
    a water-resistant polymer system wherein the water-resistant polymer system includes octylacrylamide;
    a pH sensitive polymer wherein the pH sensitive polymer includes an aqueous methacrylic polymer;
    a neutralizer; and
    an alcohol.

2. The composition of claim 1 wherein the polyvinyl lactam is poly(N-vinyl pyrrolidone).

3. The composition of claim 1 wherein the polyvinyl lactam is present in an amount of from about 1% w/v to about 10% w/v.

4. The composition of claim 1 wherein the polyvinyl lactam is present in an amount of from about 2% w/v to about 8% w/v.

5. The composition of claim 1 wherein the broad spectrum antimicrobial agent is iodine.

6. The composition of claim 1 wherein the water-resistant polymer system comprises a copolymer of octylacrylamide and a polyacrylate.

7. The composition of claim 6 wherein the copolymer of octylacrylamide and polyacrylate is present in an amount from about 0.1% w/v to about 10% w/v.

8. The composition of claim 7 wherein the copolymer of octylacrylamide and polyacrylate is present in an amount of from about 0.5% w/v to about 5% w/v.

9. The composition of claim 6 wherein the octylacrylamide is 2-ethylhexylacrylamide.

10. The composition of claim 6 wherein the polyacrylate comprises:

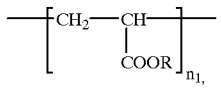

further wherein $n_1$ is selected from the integers 2 through 6000 and wherein R is selected from the group consisting of unbranched alkyl, branched alkyl, unbranched alcohol, branched alcohol, ester, ether, aryl groups, and combinations thereof.

11. The composition of claim 10 further wherein the non-aryl R substituents are selected from the group consisting of $C_1$ through $C_6$ moieties, and combinations thereof.

12. The composition of claim 11 wherein the non-aryl substituents are selected from the group consisting of $C_1$ through $C_4$ moieties, and combinations thereof.

13. The composition of claim 6 wherein the polyacrylate comprises:

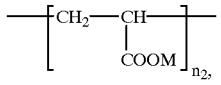

further wherein $n_2$ is from 2 through 6000 and wherein M is selected from the group consisting of Group I of the Periodic Table, and combinations thereof.

14. The composition of claim 13 further wherein M is selected from the group consisting of sodium, potassium, and combinations thereof.

15. The composition of claim 1 further comprising a polyvinyl alcohol.

16. The composition of claim 15 wherein the polyvinyl alcohol comprises:

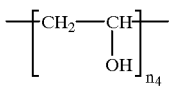

further wherein $n_4$ is selected from the integers 2 through 3400.

17. The composition of claim 15 wherein the weight average of the molecular weight of polyvinyl alcohol is between 50,000 to 150,000.

18. The composition of claim 1 further comprising a polyvinyl acetate.

19. The composition of claim 18 wherein the polyvinyl acetate comprises:

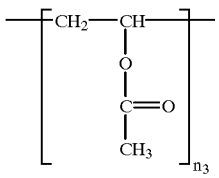

further wherein $n_3$ is selected from the integers 2 through 2100.

20. The composition of claim 18 wherein the polyvinyl acetate has a weight average molecular weight of from about 130,000 to about 180,000.

21. The composition of claim 1 further comprising a polyvinyl alcohol and a polyvinyl acetate.

22. The composition of claim 1 wherein the pH sensitive polymer is present in an amount of from about 0.1% w/v to about 10% w/v.

23. The composition of claim 22 wherein the pH sensitive polymer is present in an amount of from about 0.2% w/v to about 1% w/v.

24. The composition of claim 1 wherein the pH sensitive polymer is a copolymer of poly(methacrylic acid, methylmethacrylate).

25. The composition of claim 15 wherein the polyvinyl alcohol is present in an amount from about 0.1% w/v to about 10% w/v.

26. The composition of claim 25 wherein the polyvinyl alcohol is present in an amount from about 0.5% w/v to about 5% w/v.

27. The composition of claim 18 wherein the polyvinyl acetate is present in an amount from about 0.1% w/v to about 10% w/v.

28. The composition of claim 27 wherein the polyvinyl acetate is present in an amount from about 0.5% w/v to about 5% w/v.

29. The composition of claim 21 wherein the combination of the polyvinyl alcohol and polyvinyl acetate is present in an amount from about 0.1% w/v to about 10% w/v.

30. The composition of claim 29 wherein the combination of the polyvinyl alcohol and the polyvinyl acetate is present in an amount from about 0.5% w/v to about 5% w/v.

31. The composition of claim 1 wherein the water resistant polymer system is a neutralized carboxylated acrylic copolymer containing acrylates and octylacrylamide.

32. The composition of claim 1 wherein the water resistant polymer system is a carboxylated acrylic copolvmer of acrylates and octylacrylamide.

33. The composition of claim 1 wherein the neutralizer is selected from the group consisting of triethanolamine, 2-amino-2-methyl-1-propanol, ammonium hydroxide, potassium hydroxide, and combinations thereof.

34. An aqueous solution for use as a water resistant film-forming antimicrobial skin-preparation, the aqueous solution comprising:
PVP-I;
a water-resistant polymer system wherein the water-resistant polymer system includes octylacrylamide;
a pH sensitive polymer wherein the pH sensitive polymer includes an aqueous methacrylic polymer;
a neutralizer, and
an alcohol.

35. The composition of claim 34 wherein the PVP-I is present in an amount of from about 1 % w/v to about 10% w/v.

36. The composition of claim 35 wherein the PVP-I is present in an amount of from about 2 % w/v to about 8% w/v.

37. The composition of claim 34 wherein the water-resistant polymer system comprises a copolymer of octylacrylamide and a polyacrylate.

38. The composition of claim 37 wherein the copolymer of octylacrylamide and polyacrylate is present in an amount from about 0.1% w/v to about 10% w/v.

39. The composition of claim 38 wherein the copolymer of octylacrylamide and polyacrylate is present in an amount of from about 0.5% w/v to about 5% w/v.

40. The composition of claim 34 wherein the octylacrylamide is 2-ethylhexylacrylamide.

41. The composition of claim 37 wherein the polyacrylate comprises:

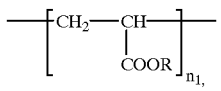

further wherein $n_1$ is selected from the integers 2 through 6000 and wherein R is selected from the group consisting of unbranched alkyl, branched alkyl, unbranched alcohol, branched alcohol, ester, ether, aryl groups, and combinations thereof.

42. The composition of claim 41 further wherein the non-aryl R substituents are selected from the group consisting of $C_1$ through $C_6$ moieties, and combinations thereof.

43. The composition of claim 42 wherein the non-aryl substituents are selected from the group consisting of $C_1$ through $C_4$ moieties, and combinations thereof.

44. The composition of claim 37 wherein the polyacrylate further comprises:

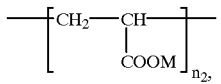

wherein $n_2$ is from 2 through 6000 and wherein M is selected from the group consisting of Group I of the Periodic Table, and combinations thereof.

45. The composition of claim 44 wherein M is selected from the group consisting of sodium, potassium, and combinations thereof.

46. The composition of claim 34 further comprising a polyvinyl alcohol.

47. The composition of claim 46 wherein the polyvinyl alcohol further comprises:

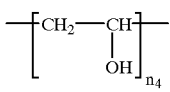

wherein $n_4$ is selected from the integers 2 through 3400.

48. The composition of claim 46 wherein the weight average of the molecular weight of polyvinyl alcohol is between 50,000 to 150,000.

49. The composition of claim 34 further comprising a polyvinyl acetate.

50. The composition of claim 49 wherein the polyvinyl acetate further comprises:

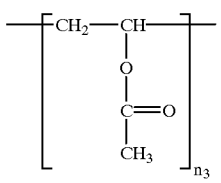

wherein $n_3$ is selected from the integers 2 through 2100.

51. The composition of claim 49 wherein the polyvinyl acetate has a weight average molecular weight of from about 130,000 to about 180,000.

52. The composition of claim 34 further comprising a polyvinyl alcohol and a polyvinyl acetate.

53. The composition of claim 34 wherein the pH sensitive polymer is present in an amount of from about 0.1% w/v to about 10% w/v.

54. The composition of claim 53 wherein the pH sensitive polymer is present in an amount of from about 0.2% w/v to about 1% w/v.

55. The composition of claim 34 wherein the pH sensitive polymer is a copolymer of poly(methacrylic acid, methylmethacrylate).

56. The composition of claim 46 wherein the polyvinyl alcohol is present in an amount from about 0.1% w/v to about 10% w/v.

57. The composition of claim 56 wherein the polyvinyl alcohol is present in an amount from about 0.5% w/v to about 5% w/v.

58. The composition of claim 49 wherein the polyvinyl acetate is present in an amount from about 0.1% w/v to about 10% w/v.

59. The composition of claim 58 wherein the polyvinyl acetate is present in an amount from about 0.5% w/v to about 5% w/v.

60. The composition of claim 52 wherein the combination of the polyvinyl alcohol and polyvinyl acetate is present in an amount from about 0.1% w/v to about 10% w/v.

61. The composition of claim 60 wherein the combination of the polyvinyl alcohol and the polyvinyl acetate is present in an amount from about 0.5% w/v to about 5% w/v.

62. The composition of claim 34 wherein the water resistant polymer system is a neutralized carboxylated acrylic copolymer of acrylates and octylacrylamide.

63. The composition of claim 34 wherein the water resistant polymer system is a carboxylated acrylic copolymer of acrylates and octylacrylamide.

64. A method for producing a film-forming topical antimicrobial composition, the method comprising the steps of: mixing together a polyvinyl lactam, a broad spectrum antimicrobial agent, an octylacrylamide, a polyacrylate, an aqueous methacrylic polymer, and an alcohol.

65. The process of claim 64 wherein the polyvinyl lactam is poly(N-vinyl pyrrolidone).

66. The process of claim 64 wherein the broad spectrum antimicrobial agent is iodine.

67. The process of claim 64 wherein the octylacrylamide is 2-ethylhexylacrylamide.

68. The process of claim 64 wherein the polyacrylate further comprises:

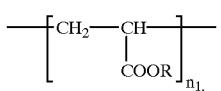

wherein $n_1$ is selected from the integers 2 through 6000 and wherein R is selected from the group consisting of unbranched alkyl, branched alkyl, unbranched alcohol, branched alcohol, ester, ether, aryl groups, and combinations thereof.

69. The process of claim 68 further wherein the non-aryl R substituents are selected from the group consisting of $C_1$ through $C_6$ moieties, and combinations thereof.

70. The process of claim 69 wherein the non-aryl substituents are selected from the group consisting of $C_1$ through $C_4$ moieties, and combinations thereof.

71. The process of claim 64 wherein the polyacrylate further comprises:

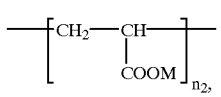

wherein $n_2$ is from 2 through 6000 and wherein M is selected from the group consisting of Group I of the Periodic Table, and combinations thereof.

72. The process of claim 71 wherein M is selected from the group consisting of sodium, potassium, and combinations thereof.

73. The process of claim 64 wherein the octylacrylamide is a polyoctylacrylamide.

74. The process of claim 64 wherein the octylacrylamide and the polyacrylate are a copolymer.

75. The process of claim 64 further comprising a polyvinyl alcohol.

76. The process of claim 75 wherein the polyvinyl alcohol further comprises:

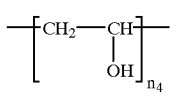

wherein $n_4$ is selected from the integers 2 through 3400.

77. The process of claim 64 further comprising a polyvinyl acetate.

78. The process of claim 77 wherein the polyvinyl acetate further comprises:

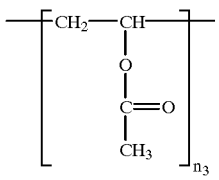

wherein $n_3$ is selected from the integers 2 through 2100.

79. The process of claim 64 further comprising a polyvinyl alcohol and a polyvinyl acetate.

80. The process of claim 64 wherein the broad spectrum antimicrobial agent is chemically complexed to the polyvinyl lactam.

81. An aqueous solution for use as a water resistant film-forming antimicrobial skin-preparation made according to the process of claim 64.

82. An aqueous solution for use as a water resistant film-forming antimicrobial skin-preparation, the aqueous solution comprising:
 a polyvinyl lactam;
 a broad spectrum antimicrobial agent chemically complexed with the polyvinyl lactam;
 a water-resistant polymer system wherein the water-resistant polymer system includes octylacrylamide;
 a pH sensitive polymer wherein the pH sensitive polymer includes an aqueous methacrylic polymer; and
 an alcohol.

83. The composition of claim 82 wherein the polyvinyl lactam is poly(N-vinyl pyrrolidone).

84. The composition of claim 82 wherein the polyvinyl lactam is present in an amount of from about 1% w/v to about 10% w/v.

85. The composition of claim 82 wherein the polyvinyl lactam is present in an amount of from about 2% w/v to about 8% w/v.

86. The composition of claim 82 wherein the broad spectrum antimicrobial agent is iodine.

87. The composition of claim 82 wherein the water-resistant polymer system comprises a copolymer of octylacrylamnide and a polyacrylate.

88. The composition of claim 87 wherein the copolymer of octylacrylamide and polyacrylate is present in an amount from about 0.1% w/v to about 10% w/v.

89. The composition of claim 88 wherein the copolymer of octylacrylamide and polyacrylate is present in an amount of from about 0.5% w/v to about 5% w/v.

90. The composition of claim 87 wherein the octylacrylamide is 2-ethylhexylacrylamide.

91. The composition of claim 87 wherein the polyacrylate further comprises:

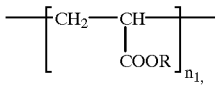

wherein $n_1$ is selected from the integers 2 through 6000 and wherein R is selected from the group consisting of unbranched alkyl, branched alkyl, unbranched alcohol, branched alcohol, ester, ether, aryl groups, and combinations thereof.

92. The composition of claim 91 further wherein the non-aryl R substituents are selected from the group consisting of $C_1$ through $C_6$ moieties, and combinations thereof.

93. The composition of claim 92 wherein the non-aryl substituents are selected from the group consisting of $C_1$ through $C_4$ moieties, and combinations thereof.

94. The composition of claim 87 wherein the polyacrylate further comprises:

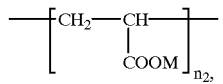

wherein $n_2$ is from 2 through 6000 and wherein M is selected from the group consisting of Group I of the Periodic Table, and combinations thereof.

95. The composition of claim 94 further wherein M is selected from the group consisting of sodium, potassium, and combinations thereof.

96. The composition of claim 82 further comprising a polyvinyl alcohol.

97. The composition of claim 96 wherein the polyvinyl alcohol further comprises:

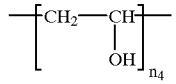

wherein $n_4$ is selected from the integers 2 through 3400.

98. The composition of claim 96 wherein the weight average of the molecular weight of polyvinyl alcohol is between 50,000 to 150,000.

99. The composition of claim 82 further comprising a polyvinyl acetate.

100. The composition of claim 99 wherein the polyvinyl acetate further comprises:

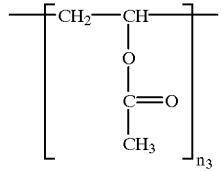

wherein $n_3$ is selected from the integers 2 through 2100.

101. The composition of claim 99 wherein the polyvinyl acetate has a weight average molecular weight of from about 130,000 to about 180,000.

102. The composition of claim 82 further comprising a polyvinyl alcohol and a polyvinyl acetate.

103. The composition of claim 82 wherein the pH sensitive polymer is present in an amount of from about 0.1% w/v to about 10% w/v.

104. The composition of claim 103 wherein the pH sensitive polymer is present in an amount of from about 0.2% w/v to about 1% w/v.

105. The composition of claim 82 wherein the pH sensitive polymer is a copolymer of poly(methacrylic acid, methylmethacrylate).

106. The composition of claim 96 wherein the polyvinyl alcohol is present in an amount from about 0.1% w/v to about 10% w/v.

107. The composition of claim 104 wherein the polyvinyl alcohol is present in an amount from about 0.5% w/v to about 5% w/v.

108. The composition of claim 99 wherein the polyvinyl acetate is present in an amount from about 0.1% w/v to about 10% w/v.

109. The composition of claim 108 wherein the polyvinyl acetate is present in an amount from about 0.5% w/v to about 5% w/v.

110. The composition of claim 102 wherein the combination of the polyvinyl alcohol and polyvinyl acetate is present in an amount from about 0.1% w/v to about 10% w/v.

111. The composition of claim 110 wherein the combination of the polyvinyl alcohol and the polyvinyl acetate is present in an amount from about 0.5% w/v to about 5% w/v.

112. The composition of claim 82 wherein the water resistant polymer system is a neutralized carboxylated acrylic copolymer of acrylates and octylacrylamide.

113. The composition of claim 82 wherein the water resistant polymer system is a carboxylated acrylic copolymer of acrylates and octylacrylamide.

114. An aqueous solution for use as a water resistant film-forming antimicrobial skin-preparation, the aqueous solution comprising:

PVP-I;

a water-resistant polymer system wherein the water-resistant polymer system includes octylacrylamide;

a sustained release polymer wherein the sustained release polymer includes copolymers of acrylic esters and methacrylic esters and the sustained release polymer further includes at least one quartemary ammonium group; and an alcohol.

115. The composition of claim 114 wherein the PVP- is present in an amount of from about 1 % w/v to about 10% w/v.

116. The composition of claim 115 wherein the PVP-I is present in an amount of from about 2 % w/v to about 8% w/v.

117. The composition of claim 114 wherein the water-resistant polymer system comprises a copolymer of octylacrylamide and a polyacrylate.

118. The composition of claim 117 wherein the copolymer of octylacrylamide and polyacrylate is present in an amount from about 0.1% w/v to about 10% w/v.

119. The composition of claim 118 wherein the copolymer of octylacrylamide and polyacrylate is present in an amount of from about 0.5% w/v to about 5% w/v.

120. The composition of claim 114 wherein the octylacrylamide is 2-ethylhexylacrylamide.

121. The composition of claim 117 wherein the polyacrylate comprises:

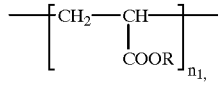

further wherein $n_1$ is selected from the integers 2 through 6000 and wherein R is selected from the group consisting of unbranched alkyl, branched alkyl, unbranched alcohol, branched alcohol, ester, ether, aryl groups, and combinations thereof.

122. The composition of claim 121 further wherein the non-aryl R substituents are selected from the group consisting of $C_1$ through $C_6$ moieties, and combinations thereof.

123. The composition of claim 122 wherein the non-aryl substituents are selected from the group consisting of $C_1$ through $C_4$ moieties, and combinations thereof.

124. The composition of claim 117 wherein the polyacrylate further comprises:

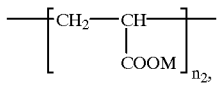

wherein $n_2$ is from 2 through 6000 and wherein M is selected from the group consisting of Group I of the Periodic Table, and combinations thereof.

125. The composition of claim 124 wherein M is selected from the group consisting of sodium, potassium, and combinations thereof.

126. The composition of claim 114 further comprising a polyvinyl alcohol.

127. The composition of claim 126 wherein the polyvinyl alcohol further comprises:

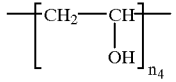

wherein $n_4$ is selected from the integers 2 through 3400.

128. The composition of claim 126 wherein the weight average of the molecular weight of polyvinyl alcohol is between 50,000 to 150,000.

129. The composition of claim 114 further comprising a polyvinyl acetate.

130. The composition of claim 129 wherein the polyvinyl acetate further comprises:

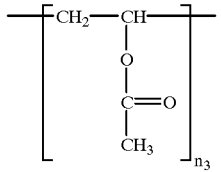

wherein $n_3$ is selected from the integers 2 through 2100.

131. The composition of claim 129 wherein the polyvinyl acetate has a weight average molecular weight of from about 130,000 to about 180,000.

132. The composition of claim 114 further comprising a polyvinyl alcohol and a polyvinyl acetate.

133. The composition of claim 114 wherein the sustained release polymer is present in an amount of from about 0.1% w/v to about 10% w/v.

134. The composition of claim 133 wherein the sustained release polymer is present in an amount of from about 0.2% w/v to about 1% w/v.

135. The composition of claim 114 wherein the sustained release polymer is a copolymer of acrylic and methacrylic esters with a low content of quaternary ammonium groups.

136. The composition of claim 126 wherein the polyvinyl alcohol is present in an amount from about 0.1% w/v to about 10% w/v.

137. The composition of claim 136 wherein the polyvinyl alcohol is present in an amount from about 0.5% w/v to about 5% w/v.

138. The composition of claim 129 wherein the polyvinyl acetate is present in an amount from about 0.1% w/v to about 10% w/v.

139. The composition of claim 138 wherein the polyvinyl acetate is present in an amount from about 0.5% w/v to about 5% w/v.

140. The composition of claim 132 wherein the combination of the polyvinyl alcohol and polyvinyl acetate is present in an amount from about 0.1% w/v to about 10% w/v.

141. The composition of claim 140 wherein the combination of the polyvinyl alcohol and the polyvinyl acetate is present in an amount from about 0.5% w/v to about 5% w/v.

142. The composition of claim 114 wherein the water resistant polymer system is a neutralized carboxylated acrylic copolymer of acrylates and octylacrylamide.

143. The composition of claim 114 wherein the water resistant polymer system is a carboxylated acrylic copolymer of acrylates and octylacrylamide.

* * * * *